United States Patent [19]

Bauer

[11] Patent Number: 4,699,902

[45] Date of Patent: Oct. 13, 1987

[54] PROCESS FOR THE PRODUCTION OF READILY SOLUBLE 5-AMINOSALICYLIC ACID PREPARATIONS

[76] Inventor: Kurt H. Bauer, Hermann-Herder-Strasse 9, 7800 Freiburg, Fed. Rep. of Germany

[21] Appl. No.: 911,105

[22] Filed: Oct. 7, 1986

Related U.S. Application Data

[60] Division of Ser. No. 759,423, Jul. 26, 1985, Pat. No. 4,632,921, which is a continuation of Ser. No. 451,975, Dec. 21, 1982, Pat. No. 4,540,685.

[30] Foreign Application Priority Data

Dec. 23, 1981 [DE] Fed. Rep. of Germany ....... 3151196

[51] Int. Cl.$^4$ ..................... A61K 31/40; A61K 31/61; A61K 31/195
[52] U.S. Cl. .................................. 514/163; 514/419; 514/561
[58] Field of Search ........................ 514/419, 163, 561

[56] References Cited

U.S. PATENT DOCUMENTS 4,211,777 7/1980 Chambers ........................... 514/169

FOREIGN PATENT DOCUMENTS

WO81/02671 10/1981 PCT Int'l Appl. .
2021409 12/1979 United Kingdom .
2059768 4/1981 United Kingdom .

*Primary Examiner*—Stanley J. Friedman
*Attorney, Agent, or Firm*—Walter H. Schneider

[57] ABSTRACT

The invention relates to a process for the production of pharmaceutical preparations based on 5-aminosalicylic acid in which the 5-aminosalicylic acid is mixed with physiologically and toxicologically acceptable, basic auxiliaries and/or buffer mixtures, which in a 1% aqueous solution give pH-values in the range from 8 to 12, and the mixture obtained is processed in known manner to form tablets, film tablets, dragees, capsules or suppositories, or in which the 5-aminosalicylic acid is mixed with a concentrated aqueous solution of the above-mentioned basic auxiliaries and/or buffer mixtures, the 5-aminosalicylic acid salt formed is precipitated, separated off from the aqueous solution and dried and the salt obtained is processed in known manner to form tablets, film tablets, dragees, capsules or suppositories.

20 Claims, No Drawings

PROCESS FOR THE PRODUCTION OF READILY SOLUBLE 5-AMINOSALICYLIC ACID PREPARATIONS

This is a division of application Ser. No. 759,423 filed July 26, 1985, now U.S. Pat. No. 4,632,921 which in turn is a continuation of application Ser. No. 451,975 filed Dec. 21, 1982, now U.S. Pat. No. 4,540,685.

This invention relates to a process for the production of readily soluble 5-aminosalicylic acid preparations.

5-aminosalicylic acid has already been tested together with 4-aminosalicylic acid (PAS) as a tuberculostatic agent, but was found to be distinctly less effective. 4-aminosalicylic acid is also considerably more stable than 5-aminosalicylic acid and, accordingly, may readily be administered—unlike 5-aminosalicylic acid—in the form of its sodium salt. Thus, it is known that the sodium salt of 4-aminosalicylic acid may be buffered with sodium carbonate and citric acid and coated with a film resistant to stomach juices (cf. W. A. Ritschel, die Tablette 1966, pages 47/48).

Hitherto, salazosulfapyridine has been used for treating *Colitis ulcerosa* and Crohn's disease. In the intestine, this substance is split by bacteria or enzymes into 5-aminosalicylic acid and into the sulfonamide, sulfapyramidine. For some time, it was not known which of the three substances was the active agent. Recent studies have shown that 5-aminosalicylic acid is the effective constituent whereas the sulfapyramidine is mainly responsible for side effects. 5-aminosalicylic acid has hitherto been regarded as therapeutically ineffectual (Hagers Handbuch der Pharmazeutischen Praxis, 4th New Edition, second volume, 1969, pages 1023, 1026). Experimental therapy has already been carried out with 5-aminosalicylic acid in the form of suppositories and enemas. However, suppositories and, in particular, enemas are unpleasant to use, the administration of enemas in particular being particularly time-consuming. Tests with tablets have hitherto been unsuccessful. Accordingly, on account of its poor solubility and/or poor stability, 5-aminosalicylic acid has never been successfully used in practice. For these reasons, 5-aminosalicylic acid has in the past always been used in the form of salazosulfapyridine and, even today, salazosulfapyridine is still used in the field of therapy. It is assumed that, during its splitting in the large intestine, 5-aminosalicylic acid accumulates in statu nascendi in very finely divided form, i.e. in a state of dispersion which could not be achieved mechanically by grinding, and becomes active in this way.

5-aminosalicylic acid (5-amino-2-hydroxybenzoic acid) is substantially or completely insoluble in the most commonly used solvents. Because of this, it is virtually impossible in this way to incorporate the compound in molecular dispersion to guarantee good or appropriate bio-availability. It is only in strong alkalis that 5-aminosalicylic acid shows sufficient solubility for this purpose. Under these conditions, however, it is extremely unstable. At pH-values above 10 to 12, the 5-aminosalicylic acid changes colour to deep brown within a few minutes.

OBJECT OF THE INVENTION

Accordingly, the object of the present invention is to provide a process by which 5-aminosalicylic acid can be incorporated in pharmaceutical preparations and in which no intolerable stability problems arise. After administration, the 5-aminosalicylic acid is intended to be released from the pharmaceutical preparation in dissolved or very finely divided form at the place where it is to develop its effect. The process is intended to be able to be carried out easily and to enable 5-aminosalicylic acid to be applied in the form of tablets, dragees, capsules etc.

EXPLANATION OF THE INVENTION

The present invention relates to a process for the production of readily soluble pharmaceutical preparations based on 5-aminosalicylic acid which is characterized in that the 5-aminosalicylic acid is mixed with physiologically and toxicologically acceptable, basic auxiliaries and/or buffer mixtures, which in a 1% aqueous solution give pH-values in the range from 8 to 12, and in that the mixture obtained in processed in known manner to form tablets, film tablets, dragees, capsules or suppositories, or in that the 5-aminosalicylic acid is mixed with a concentrated aqueous solution of physiologically and toxicologically acceptable, basic auxiliaries and/or buffer mixtures, which in a 1% aqueous solution give pH-values in the range from 8 to 12, the 5-aminosalicylic acid salt formed is precipitated with a suitable water-miscible solvent, separated off from the aqueous solution, dried and the salt obtained processed in known manner to form tablets, film tablets, dragees, capsules or suppositories.

DETAILED DESCRIPTION OF THE INVENTION

The basic auxiliaries or buffer mixtures used in the process according to the invention are those which, in a 1% aqueous solution, have pH-values in the range from 8 to 12 and preferably in the range from 9 to 11. In principle, it is possible to use any inorganic and organic compounds or buffer mixtures which are sufficiently stable and sufficiently soluble in water, which produce the above-mentioned pH-values in the aqueous solution and which are physiologically acceptable as auxiliaries, i.e. which may be taken internally without any significant effects or side effects.

Basic auxiliaries or buffer mixtures such as these include in general alkali and some alkaline-earth compounds, particularly alkali and alkaline-earth salts, alkali hydroxides, such as for example sodium or potassium hydroxide, alkali carbonates, such as sodium or potassium carbonate, alkali bicarbonates, such as sodium or potassium bicarbonate, ammonium hydroxide, ammonium carbonates and ammonium bicarbonates and also alkali phosphates and hydrogen phosphates.

Preferred alkaline auxiliaries are sodium carbonate, sec.-sodium phosphate, sec.-sodium phosphate in admixture with tert.-sodium phosphate, sodium hydroxide in combination with glycine, sodium carbonate, sodium bicarbonate and mixtures of sodium carbonate and sodium bicarbonate, ammonia, ammonium chloride and also a mixture of ammonia and ammonium chloride, calcium hydroxide and also a mixture of calcium hydroxide and glycine, sodium glycerol phosphate. It is also possible to use salts of organically compatible acids, such as salts of citric acid, tartaric acid etc., for example trisodium citrate, disodium tartrate. Instead of using the sodium salts, it is also possible to use the potassium salt. Another preferred mixture is a mixture of sodium carbonate and glycine.

Other suitable basic auxiliaries are organic compounds, such as ethanolamine (cholamine), diethanolamine, triethanolamine, tri-(hydroxymethyl)-aminomethane (tris-buffer, THAM), N-methyl glucamine, lysine, arginine, choline etc. Of the organic compounds, ethanolamine, tri-(hydroxymethyl)-aminomethane, N-methyl glucamine, lysine, arginine and choline are preferred.

Other favourable qualifications for application include authorization for use as a food additive, as a pharmaceutical auxiliary or at least as a harmless auxiliary, a low molecular weight (so that for example the tablets do not become too large), ready availability and a reasonable price.

In the first alternative of the process according to the invention, the 5-aminosalicylic acid is dry-mixed with the alkaline auxiliary and/or buffer mixtures and, optionally, solid pharmaceutical vehicles and standard additives and the resulting mixture briquetted in known manner. The briquettes thus obtained are then size-reduced in known manner to form a granulate, for example a granulate having an average particle size in the range from 0.6 mm to 1.5 mm and preferably in the range from 0.8 mm to 1.0 mm. This granulate is particularly suitable for the production of tablets, dragee cores or capsules containing from 200 mg to 900 mg of 5-aminosalicylic acid per pharmaceutical formulation unit. In cases where solid pharmaceutical formulations containing relatively low doses, for example from 30 mg to 175 mg per tablet or capsule, are produced, the granulates have to be sieved more finely, i.e. to average particle sizes of from 0.15 mm to 0.5 mm. The granulates may be processed in conjunction with standard auxiliaries to form tablets, dragees, capsules etc. Granulates intended for direct application, i.e. granulates which are not converted into tablet form, have to be sieved to a particle size of larger than 1.5 mm.

However, the 5-aminosalicylic acid may also be mixed together with the physiologically and toxicologically acceptable basic auxiliaries and a pharmaceutically acceptable liquid vehicle. Suitable liquid vehicles are any of the vehicles normally used.

Examples of solid vehicles are microcrystalline cellulose, cellulose powder, carboxymethyl cellulose, methyl cellulose, starch, lactose, sucrose, dicalcium phosphate, calcium sulfate etc.

Examples of liquid vehicles are anhydrous oils (triglycerides), paraffin oil, polyethylene glycols having molecular weights of from 300 to 600, glycerol, propylene glycol, etc. These liquid vehicles are also suitable for use inter alia as vehicles for filling soft gelatin capsules with 5-aminosalicylic acid.

The concentration of the basic auxiliaries or of the buffer mixtures is generally in the range from 0.5- to 3-molar and preferably in the range from 1- to 1.5-molar, based on the 5-aminosalicylic acid. Processing of the mixture of 5-aminosalicylic acid and the basic auxiliary or buffer mixturs to form the pharmaceutical preparation is carried out in the absence of water. If necessary, the pharmaceutical preparation may be provided in known manner with a coating resistant to stomach juices, should this be therapeutically appropriate. This ensures that the effectiveness of the buffer is not impaired by the effect of the acidic stomach juices.

On coming into contact in the intestine with physiological liquids which either diffuse into pharmaceutical preparations of the type in question or, after dissolution of the coating, permeate through the content of the particular pharmaceutical formulation, the auxiliary or buffer mixtures are initially dissolved. The 5-aminosalicylic acid dissolves relatively quickly at the resulting pH-values which, for reasons of stability, should be far below pH 12.

In the second alternative of the process according to the invention, the 5-aminosalicylic acid is mixed with a concentrated aqueous solution of the above-described basically reacting auxiliaries and/or buffer mixtures and the resulting mixture converted into sufficiently stable and rapidly dissolving salt. To this end, the auxiliaries and/or buffer mixtures are dissolved in as high a concentration as possible in water, preferably in the absence of light and with cooling. Preferably, more than 1 part of auxiliary and/or buffer mixture is dissolved in 2 parts of water. The resulting solution is mixed with the 5-aminosalicylic acid, preferably in the absence of light and with cooling. Mixing is preferably carried out with stirring. The 5-aminosalicylic acid dissolves in the alkaline-reacting solution and forms a salt. A water-miscible solvent is then added to the resulting solution, preferably with stirring and cooling and again in the absence of light, in order to precipitate the corresponding 5-aminosalicylic acid salt. Suitable water-miscible solvents are, for example, alcohols, such as methanol, ethanol or propanol, or ketones, such as acetone, methyl ethyl ketone, or tetrahydrofuran (THF) or dimethyl formamide (DMF) or dimethyl acetamide (DMA) or various glycol ethers, etc. The solvent is preferably introduced in a single addition over a period of a few minutes. The solution is then cooled to below 8° C. and, if necessary, seed crystals are added. Thereafter the corresponding 5-aminosalicylic acid salt is precipitated and is separated off as quickly as possible from the mother liquor and dried.

The readily water-soluble salt obtained may be processed in known manner with or without pharmaceutical vehicles of the type mentioned above and optionally using standard auxiliaries to form a variety of pharmaceutical preparations. For example, it is possible as mentioned above to prepare tablets, film tablets, dragees, capsules and suppositories using the salts. If necessary, these pharmaceutical preparations may also be provided with a coating resistant to stomach juices.

The standard dose for tablets and suppositories is currently between 250 mg and 500 mg (for both). The daily dose amounts to between 2 and 4 g. It is possible that these doses may be reduced by the molecularly disperse distribution. However, this may first be established by clinical trials.

The invention is illustrated but in no way limited by the following Examples:

EXAMPLE 1

150.0 g of glycine are intensively mixed with 50.0 g of 30% sodium hydroxide and the resulting mixture heated for 10 minutes on a water bath. 15.0 g of water are then removed from this mixture by drying. The dry powder formed is stirred homogeneously with 500.0 g of 5-aminosalicylic acid in the absence of light into an approximately 1500.0 g of solid fat (bases for suppositories) melted at 50° to 60° C. The resulting mixture is poured in the usual way into suppository moulds at 40° to 50° C., resulting in the formation of 1000 suppositories each having a gross weight of 2.0 g and containing 500 mg of 5-aminosalicylic acid.

EXAMPLE 2

11.0 kg of sodium carbonate are briquetted in known manner with 1.0 kg of sodium bicarbonate, 25.0 kg of 5-aminosalicylic acid and 4.75 kg of cellulose powder and the briquettes obtained subsequently size-reduced to a granulate having an average particle size of 0.8 mm. 0.75 kg of wheat starch and 0.5 kg of magnesium stearate are added to the resulting granulate as outer phase, followed by pressing in suitable tablet presses to form tablets having a gross weight of 0.430 g.

Approximately 100,000 tablets each containing 250 mg of 5-aminosalicylic acid are obtained. The tablets are provided in known manner with a protective coating of methyl cellulose and, finally, are coated with a layer of cellulose acetate phthalate film resistant to stomach juices.

EXAMPLE 3

4.5 kg of potassium carbonate, 1.0 kg of glycine, 6.25 kg of 5-aminosalicylic acid and 2.5 kg of spray-dried dicalcium phosphate are homogeneously mixed and compacted by means of a calender roll. The shells obtained are forced through a 1 mm mesh sieve after which 0.5 kg of cornstarch and 0.25 kg of stearic acid powder are added as external phase to the resulting tableting mixture. The tableting mixture is then pressed in suitable tableting machines to form approximately 50,000 dragee cores each weighing 300 mg. The dragee cores thus obtained each contain 125 mg of 5-aminosalicylic acid. They are coated in known manner with a film of Eudragit S ® (=anionic polymer of methacrylic acid and methyl methacrylate) resistant to stomach juices and, finally, made up into dragees using a suspension of sugar.

EXAMPLE 4

10.0 kg of 5-aminosalicylic acid and 10.0 kg of ammonium carbonate are suspended in 20.0 kg of a mixture of vegetable oil and wax. The suspension is homogenized on a three-roll stand and subsequently introduced into soft gelatin capsules in such a quantity that each capsule contains 250 mg of 5-aminosalicylic acid. Finally, the soft gelatin capsules are hardened by treatment with an organic aldehyde solution which makes them resistant to stomach juices.

EXAMPLE 5

0.765 kg of 5-aminosalicylic acid are dissolved in 1.462 kg of a 50% aqueous L-lysine solution by gentle heating in the absence of light. After the addition of approximately 1 litre of ethanol, followed by cooling, a readily water soluble salt is precipitated and is filtered off under suction and washed with acetone. After drying, the pale pink coloured salt may be incorporated in virtually any required dosage in a variety of different pharmaceutical formulations.

EXAMPLE 6

153.1 g of 5-aminosalicylic acid are dissolved in the absence of light in 50 to 70% aqueous solutions, which contain for example either 195.2 g of N-methyl glucamine or 121.1 g of tris-(hydroxymethane)-methylamine or 121.2 g of choline, and subsequently dried in vacuo. The salts thus obtained are washed with acetone or with an alcohol and dried. They are readily soluble in water and are so stable that they may be incorporated without difficulty in pharmaceutical formulations.

I claim:

1. A process for preparing a stable and readily soluble pharmaceutical preparation for oral or rectal application based on 5-aminosalicylic acid for use in the treatment of Crohn's disease and ulcerative colitis which comprises mixing (1) a pharmaceutically acceptable solid or liquid carrier and (2) a dry mixture of 5-aminosalicylic acid and a pharmaceutcally acceptable alkaline material, selected from alkali and alkaline earth metal hydroxides, phosphates and citrates and mixtures thereof, said pharmaceutically acceptable alkaline material giving a pH of 8-12 in a 1.0% aqueous solution and being present in the dry mixture in a concentration of 0.5-3.0 mols per mol of 5-aminosalicylic acid.

2. A process according to claim 1 in which the concentration of said pharmaceutically acceptable alkaline material is 0.5-1.5 mols per mol of 5-aminosalicylic acid.

3. A process according to claim 1 in which the pharmaceutically acceptable alkaline material is sodium hydroxide.

4. A process according to claim 1 in which the pharmaceutically acceptable alkaline material is sec. sodium phosphate.

5. A process according to claim 1 in which the pharmaceutically acceptable alkaline material is a mixture of sec. sodium phosphate and tert. sodium phosphate.

6. A process according to claim 1 in which the pharmaceutical preparation suitable for oral application is provided with a coating resistant to stomach juices.

7. A stable and readily soluble pharmaceutical preparation for oral or rectal application based on 5-aminosalicylic acid for use in the treatment of Crohn's disease and ulcerative colitis which comprises (1) a pharmaceutically acceptable solid or liquid carrier and (2) a dry mixture comprising 5-aminosalicylic acid and a pharmaceutically acceptable alkaline material selected from alkali and alkaline earth metal hydroxides, phosphates and citrates, said pharmaceutically acceptable alkaline material giving a pH of 8-12 in a 1.0% aqueous solution and being present in the dry mixture in a concentration of 0.5-3.0 mols per mol of 5-aminosalicylic acid.

8. A preparation according to claim 7 in which the concentration of pharmaceutically acceptable alkaline material is 0.5-1.5 mols per mol of 5-aminosalicylic acid.

9. A preparation according to claim 1 in which the pharmaceutically acceptable alkaline material is sodium hydroxide.

10. A preparation according to claim 1 in which the pharmaceutically acceptable alkaline material is sec. sodium phosphate.

11. A preparation according to claim 1 in which the pharmaceutically acceptable alkaline material is a mixture of sec. sodium phosphate and tert. sodium phosphate.

12. A preparation according to claim 1 in which the pharmaceutical preparation suitable for oral application is provided with a coating resistant to stomach juices.

13. A method for treating Crohn's disease and ulcerative colitis in humans which comprises orally or rectally administering a preparation according to claim 7.

14. A method for treating Crohn's disease and ulcerative colitis in humans which comprises orally or rectally administering a preparation according to claim 8.

15. A method for treating Crohn's disease or ulcerative colitis in humans which comprises orally or rectally administering a preparation according to claim 9.

16. A method for treating Crohn's disease and ulcerative colitis in humans which comprises orally or rectally administering a preparation according to claim 10.

17. A method for treating Crohn's disease and ulcerative colitis in human which comprises orally or rectally administering a preparation according to claim 11.

18. A method for treating Crohn's disease and ulcerative colitis in human which comprises orally administering a preparation according to claim 12.

19. A stable and readily soluble pharmaceutical preparation for oral or rectal application based on 5-aminosalicylic acid for use in the treatment of Crohn's disease and ulcerative colitis prepared in accordance with claim 1.

20. A stable and readily soluble pharmaceutical preparation for oral application based on 5-aminosalicylic acid for use in the treatment of Crohn's disease and ulcerative colitis prepared in accordance with claim 6.

* * * * *